(12) United States Patent  
Kokubun et al.

(10) Patent No.: US 8,055,045 B2  
(45) Date of Patent: Nov. 8, 2011

(54) METHOD AND SYSTEM FOR COLLECTING IMAGE DATA FROM IMAGE DATA COLLECTION RANGE INCLUDING PERIODICALLY MOVING PART

(75) Inventors: Hiroto Kokubun, Kashiwa (JP); Osamu Miyazaki, Moriya (JP); Tetsuo Nakazawa, Nagareyama (JP)

(73) Assignee: Hitachi Medical Corporation, Tokyo (JP)

( * ) Notice: Subject to any disclaimer, the term of this patent is extended or adjusted under 35 U.S.C. 154(b) by 1020 days.

(21) Appl. No.: 10/593,359

(22) PCT Filed: Mar. 11, 2005

(86) PCT No.: PCT/JP2005/004305  
§ 371 (c)(1),  
(2), (4) Date: Sep. 18, 2006

(87) PCT Pub. No.: WO2005/089651  
PCT Pub. Date: Sep. 29, 2005

(65) Prior Publication Data  
US 2008/0056547 A1 Mar. 6, 2008

(30) Foreign Application Priority Data

Mar. 19, 2004 (JP) .................................. 2004-080939  
Apr. 5, 2004 (JP) .................................. 2004-110756

(51) Int. Cl.  
*G06K 9/00* (2006.01)

(52) U.S. Cl. ............. 382/131; 382/128; 382/132; 378/4; 378/8; 378/95; 600/407; 600/413; 600/425; 600/428; 600/508

(58) Field of Classification Search ................. 378/4, 8, 378/15, 95; 382/131, 132, 128, 154; 600/425, 600/410  
See application file for complete search history.

(56) References Cited

U.S. PATENT DOCUMENTS  
6,504,894 B2   1/2003 Pan et al.  
(Continued)

FOREIGN PATENT DOCUMENTS  
JP   4-22344   1/1992  
(Continued)

OTHER PUBLICATIONS

HeartView CT Application Guide by Siemens Medical, Software Version syngo CT 2005A, © 2002-2004, Siemens AG Order No. C2-023.630.11.03.02 Printed in Germany Sep. 2004.*

(Continued)

*Primary Examiner* — Sath V Perungavoor  
*Assistant Examiner* — Jason Heidemann  
(74) *Attorney, Agent, or Firm* — Cooper & Dunham LLP

(57) ABSTRACT

A method includes a periodic motion data input step S208 of receiving input of periodic motion data indicating changes of the periodic motion with time in an object to be examined who is a target of image data collection, a step S214 of estimating fluctuations in the time resolution of the image data with time based on the periodic motion data, designating an image collection range in the object, and adjusting the collection position of the image data such that the image data is collected in the image collection range at a suitable time of image data collection, the estimated time resolution being set in a predetermined suitable range, and an image data collection position control step S216 of relatively moving at least a part of the image data collection range and the collection position of the image data such that the part of the range and the position are superimposed on each other within a time when the image data of the image data collection range has a time resolution within the desired range based on the image data collection conditions.

16 Claims, 12 Drawing Sheets

U.S. PATENT DOCUMENTS

| | | | |
|---|---|---|---|
| 6,522,712 B1* | 2/2003 | Yavuz et al. | 378/4 |
| 6,539,074 B1* | 3/2003 | Yavuz et al. | 378/4 |
| 6,556,697 B1* | 4/2003 | Bruder et al. | 382/131 |
| 7,006,862 B2* | 2/2006 | Kaufman et al. | 600/523 |
| 7,142,703 B2* | 11/2006 | Kaufman et al. | 382/131 |
| 7,209,779 B2* | 4/2007 | Kaufman et al. | 600/425 |
| 7,251,308 B2* | 7/2007 | Tsuyuki | 378/8 |
| 7,308,299 B2* | 12/2007 | Burrell et al. | 600/428 |
| 7,421,057 B2* | 9/2008 | Watanabe | 378/8 |
| 2003/0161435 A1* | 8/2003 | Ozaki | 378/4 |
| 2003/0163039 A1* | 8/2003 | Pan et al. | 600/425 |
| 2004/0254447 A1* | 12/2004 | Block et al. | 600/410 |
| 2005/0058238 A1* | 3/2005 | Flohr et al. | 378/8 |
| 2005/0100126 A1* | 5/2005 | Mistretta et al. | 378/15 |
| 2005/0111622 A1* | 5/2005 | Bruder et al. | 378/95 |
| 2005/0111623 A1* | 5/2005 | Bruder et al. | 378/95 |

FOREIGN PATENT DOCUMENTS

| | | |
|---|---|---|
| JP | 10-216122 | 8/1998 |
| JP | 2000-189412 | 7/2000 |
| JP | 2000-296120 | 10/2000 |
| JP | 2000-325335 | 11/2000 |
| JP | 2001-212137 | 8/2001 |
| WO | WO02/26135 | 4/2002 |

OTHER PUBLICATIONS

English machine translation of JP 2001-212137, generated on Feb. 19, 2011, pp. 1-11.*

International Preliminary Report On Patentability in connection with International Appln. No. PCT/JP2005/004305.

* cited by examiner

FIG. 10

| Scanning Practice is underway ||
|---|---|
| State of progress | Precautions |
| Preparation for scanning | • Gantry is moving. You will feel small vibrations.<br>• Gantry is rotating. You will hear a large sound. |
| Contrast imaging | • Contrast imaging is starting. You will feel hot. |
| Scanning | • Scanning is starting. Prepare for breath holding. |
| Scanning completed | • Scanning is completed. Please wait for a while. |

⇐ Scanning steps in progress

FIG. 11

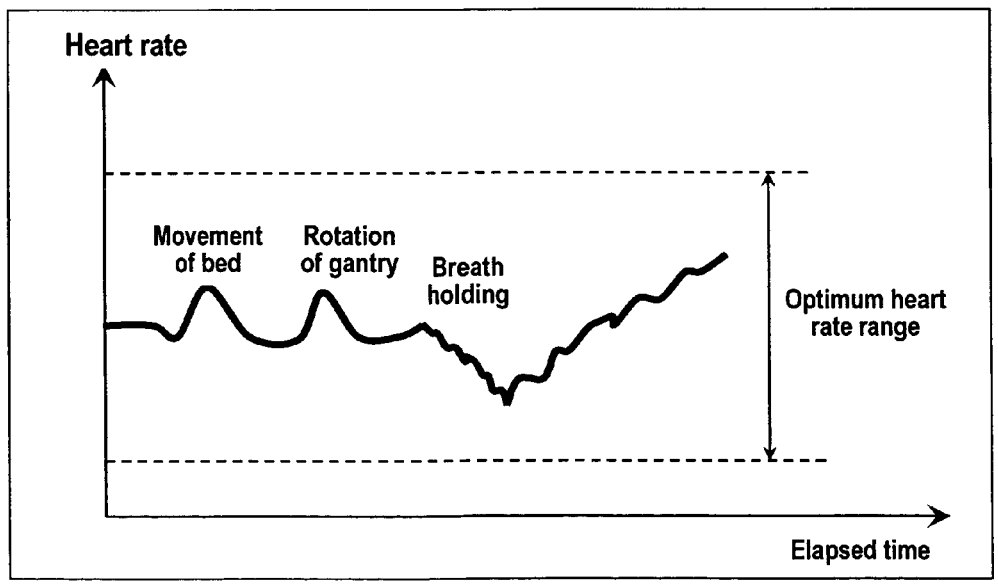

FIG. 12
| ID | Name | Breath holding time | Tendency of fluctuations in heart rate | | |
|---|---|---|---|---|---|
| | | | Breath holding | Contrast imaging | Fluctuations in heart rate in previous scanning |
| 0001 | Name1 | 40s | ↑ Up | - Stay | 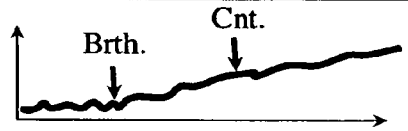 Brth. Cnt. |
| 0002 | Name2 | 35s | - Stay | ↑ Up | 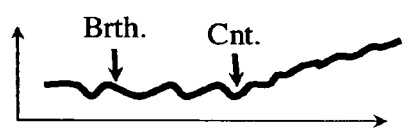 Brth. Cnt. |
| 0003 | Name3 | 55s | ↓ Down | - Stay | 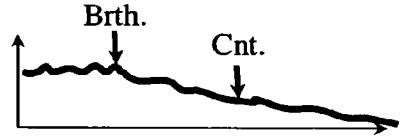 Brth. Cnt. |
| ... | ... | ... | ... | ... | ... |

FIG. 13

| ID | Name | Number of times of scanning heart | Average breath holding time | Tendency of fluctuations in heart rate due to breath holding | | | | Tendency of fluctuations in heart rate due to contrast imaging | | | |
|---|---|---|---|---|---|---|---|---|---|---|---|
| | | | | Up | Stay | Down | Average of fluctuations | Up | Stay | Down | Average of fluctuations |
| 001 | Name1 | 3 | 40s | 2 | 1 | 0 | +10 | 0 | 3 | 0 | 0 |
| 002 | Name2 | 5 | 35s | 1 | 4 | 0 | +2 | 3 | 2 | 0 | +5 |
| 003 | Name3 | 7 | 55s | 0 | 3 | 4 | -10 | 1 | 6 | 0 | +1 |
| ... | ... | ... | ... | ... | ... | ... | ... | ... | ... | ... | ... |

METHOD AND SYSTEM FOR COLLECTING IMAGE DATA FROM IMAGE DATA COLLECTION RANGE INCLUDING PERIODICALLY MOVING PART

TECHNICAL FIELD

The present invention relates to an image data collection control method and an image data collection system and particularly relates to an image data collection control method and an image data collection system which reduce motion artifact caused by a heartbeat in a cardiac area.

BACKGROUND ART

When image data is collected from the heart area of an object to be examined and an image is reconstructed based on the data, the image quality is degraded by cardiac motion artifact caused by a heartbeat and respiratory motion artifact caused by a thorax motion associated with respiration.

Conventionally, a scanning method called electrocardiographic synchronous scanning or ECG (electro cardio gram) is available in which electrocardiographic data is obtained to reduce heartbeat motion artifact, and then image data is collected and an image is reconstructed based on the data in synchronization with a heartbeat or with a phase shift relative to a heartbeat (for example, Patent document 1). For example, according to segment reconstruction which is a kind of cardiographic synchronous scanning, based on cardiographic data recorded with image data, image data collected in a diastole during which cardiac motions are relatively few is extracted and an image is reconstructed according to the data, so that an image can be obtained with a preferable time resolution and less cardiac motion artifact. During the collection of image data, image data collection conditions such as a scanning speed are set and fixed according to the heart rate of an object to be examined. Thus it is desirable to stabilize the heart rate to keep the high quality of an obtained image.

In order to prevent respiratory motion artifact, the object is generally caused to hold his/her breath to prevent a thorax motion during the collection of image data.

Patent document 1: Japanese Patent Application Laid-Open No. 2000-189412

However, in many cases, when the object holds his/her breath, the heart rate tends to fluctuate more than a resting pulse rate. Although fluctuations in heart rate due to breath holding vary among individuals, the fluctuations vary, in any event, the time resolution of an image obtained in cardiographic synchronous scanning. For example, in the case of image data collection conditions set suitably for a resting heart rate, when the heart rate during the collection of image data is almost equal to the resting heart rate, an image obtained under the image data collection conditions has a preferable and constant time resolution. In reality, however, the heart rate during the collection of image data deviates from the resting heart rate, and thus a satisfactory image cannot be obtained under image data collection conditions suitable for the resting heart rate.

The present invention is devised in view of such circumstances. An object of the present invention is to provide an image data collection control method and an image data collection system whereby preferable image data can be obtained even when the heart rate of an object to be examined fluctuates during the collection of image data.

BRIEF SUMMARY

In an aspect of this disclosure, there is provided an image data collection control method for collecting multiple pieces of image data from an image data collection range including a periodically moving part of an object to be examined, the method including: a periodic motion data obtaining step of obtaining periodic motion data indicating changes of a periodic motion with time, an image data collection condition setting step of setting image data collection conditions for allowing the image data of the image data collection range to have a time resolution within a desired range, an image data collection position control step of relatively moving at least a part of the image data collection range and the collection position of the image data such that the part of the range and the collection position are superimposed on each other within a time when the image data of the image data collection range has a time resolution within the desired range based on the image data collection conditions, and an image data collecting step of collecting the image data of at least a part of the image data collection range on the image data collection position.

In another aspect of this disclosure, there is provided an image data collection system for collecting multiple pieces of image data from an image data collection range including a periodically moving part of an object to be examined, the system comprising: a periodic motion data obtaining means for obtaining periodic motion data indicating changes of a periodic motion with time, an image data collection condition setting means for setting image data collection conditions for allowing the image data of the image data collection range to have a time resolution within a desired range, an image data collection position control means for relatively moving at least a part of the image data collection range and the collection position of the image data such that the part of the range and the collection position are superimposed on each other within a time when the image data of the image data collection range has a time resolution within the desired range based on the image data collection conditions, and an image data collecting means for collecting the image data of at least a part of the image data collection range on the image data collection position.

In another aspect, changes of periodic motion on a periodically moving part of an object are estimated during the collection of image data, and the collection of image data is controlled accordingly, so that image data can be collected with a preferable time resolution.

BRIEF DESCRIPTION OF THE DRAWINGS

FIG. 10 is a schematic diagram showing an example of a screen presented by heart rate fluctuation factor presenting means;

FIG. 11 is a schematic diagram showing an example of fluctuations in heart rate presented by the heart rate fluctuation factor presenting means;

FIG. 12 is a schematic diagram showing an example of heart rate information registered by the heart rate information registering means;

FIG. 13 is a schematic diagram showing an example of heart rate information registered by the heart rate information presenting means;

FIG. 15(*b*) is a schematic diagram showing an example of the body movement navigation sequence.

DESCRIPTION OF THE SYMBOLS

Figure 1:
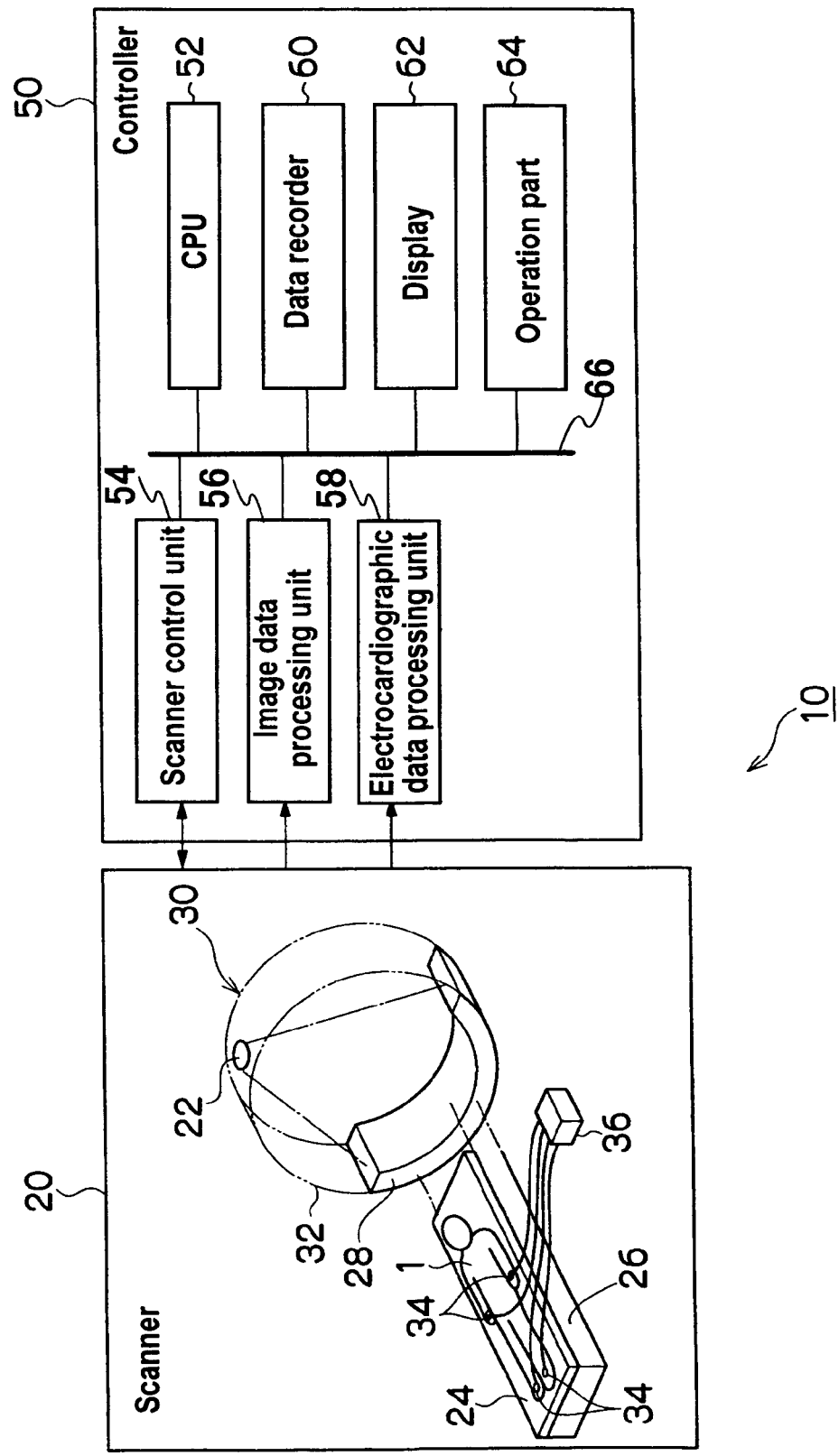
FIG. 1 is a schematic structural diagram showing an embodiment of an image data collection system according to the present invention.

1 object
10 image data collection system
20 scanner
22 X-ray generator
24 object table
26 object table moving device
28 X-ray detector
30 scanner body
32 scanner rotating device
34 electrocardiographic electrode
36 electrocardiographic data acquisition device
50 controller
52 CPU
54 scanner control unit
56 image processing unit
58 electrocardiographic data processing unit
60 data recorder
62 display
64 operation part
66 bus
E image data collection end marker
G time resolution graph
I image collection range marker
N numerical display
P projected image
R recommended range marker
S image data collection start marker
101 X-ray tube
102 scanner gantry
203 object table
104 X-ray detector
105 display
106 periodic motion data recording means (electrocardiograph)
107 image processing device
108 rotary disc
109 collimator
110 rotary drive
111 measurement control unit
112 computer (controller)
113 input device
114 scanning information transfer unit
115 storage device
201 magnet
202 object
203 bed
204 RF coil
205 gradient magnetic field generating coil
206 gradient magnetic field generating coil
207 gradient magnetic field generating coil
208 high frequency power supply
209 gradient magnetic field power supply
210 gradient magnetic field power supply
211 gradient magnetic field power supply
212 synthesizer
213 modulation circuit
214 amplifier
215 receiver
216 sequencer
217 storage device
218 calculator
219 display

BEST MODE FOR CARRYING OUT THE INVENTION

The following will describe preferred embodiments of an image data collection system of the present invention in accordance with the accompanying drawings.

Embodiment 1

FIG. 1 is a schematic structural diagram showing an image data collection system according to an embodiment of the present invention. As shown in FIG. 1, the image data collection system 10 is mainly made up of a scanner 20 for collecting scanning data from an object to be examined 1, and a controller 50 for controlling the overall image data collection system 10 and the arithmetic operations of data having been collected by the scanner 20.

The scanner 20 can be any type as long as scanning data is collected from the object 1. Devices using X-rays, infrared rays, ultrasonic waves, nuclear magnetic resonance, positron emission, irradiation from a radioisotope, and so on are generally used. The following will discuss an X-ray CT apparatus as an example.

The scanner 20 mainly includes an X-ray generator 22 for generating X-rays, an object table 24 on which the object 1 is laid, an object table moving device 26 for moving the object table 24 along the body axis (hereinafter, simply will be referred to as "body axis"), an X-ray detector 28 for detecting X-rays having passed through the object 1, a scanner rotating device 32 for continuously rotating, about the body axis, a scanner body 30 including the X-ray generator 22 and the X-ray detector 28, and an electrocardiographic data acquisition device 36 for acquiring electrocardiographic data on the object 1 through electrocardiographic electrodes 34 making contact with the body surface of the object 1.

The controller 50 mainly includes a CPU 52 for controlling the overall image data collection system 10, a scanner control unit 54 for controlling the scanner 20, an image data processing unit 56 for processing image data having been obtained by the X-ray detector 28, an electrocardiographic data processing unit 58 for processing electrocardiographic data having been obtained by the electrocardiographic data acquisition device 36, a data recorder 60 for storing various kinds of data, a display 62 for displaying various images, an operation part 64 including a pointing device such as a keyboard, a mouse, and a trackball and input means such as a touch panel, and a bus 66 for mediating data transmission and reception of the units in the image data collection system 10. The data recorder 60 may be a memory included or installed outside the controller 50, a storage device such as a magnetic disc, a device for writing and reading data on removable external media, and a device for transmitting and receiving data through an external storage device and a network, and so on. The data recorder 60 stores, in the CPU 52, a program for controlling the image data collection system 10.

Figure 2:
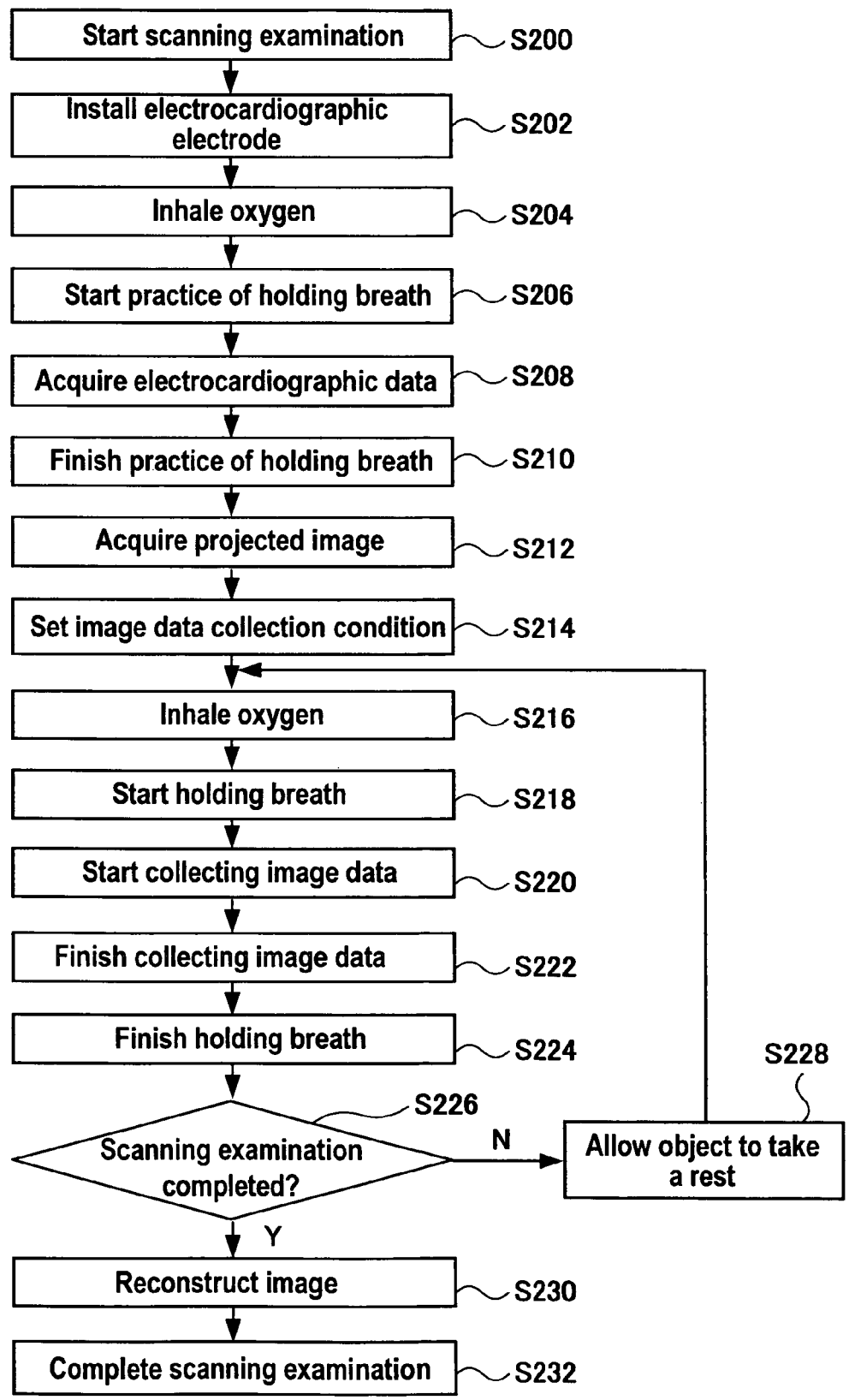
FIG. 2 is a flowchart showing the flow of a series of cardiac area scanning examinations conducted by the image data collection system of FIG. 1.

FIG. 2 is a flowchart showing the flow of a series of cardiac area scanning examinations conducted by the image data collection system 10 of the present embodiment. First, the object 1 is laid on the object table 24 and the scanning examination is started (S200). The electrocardiographic electrodes 34 are attached to the body surface of the object 1 to obtain electrocardiographic data on the object 1 (S202).

In order to prevent respiratory motion artifact, the object 1 has to hold his/her breath during the collection of image data. Thus the object 1 practices holding his/her breath before the collection of image data. In order to allow the object 1 to stably hold his/her breath as long as possible, the object 1 preferably inhales air with a high content of oxygen (S204) beforehand. This step may be omitted in some cases. After that, the object 1 is caused to hold his/her breath (S206); meanwhile the electrocardiographic data acquisition device 36 acquires, through the electrocardiographic electrodes 34, electrocardiographic data including the electrocardiographic waveform and heart rate of the object 1 (S208). The obtained electrocardiographic data is processed by the electrocardiographic data processing unit 58 and recorded in the data recorder 60.

At the completion of the practice of holding his/her breath (S210), a projected image of the object 1 is acquired (S212). Then, based on the electrocardiographic data having been obtained in S208 during the practice of holding his/her breath and the projected image having been obtained in S212, image data collection conditions are set which include an elapsed time (called delay time) from a start time of breath holding to a start time of image data collection, a starting position of image data collection, an end position of image data collection, a scanning speed, and an amount of the movement of the object table (S214). The conditions may be automatically set by the CPU 52 according to a predetermined program or set by an operator by means of the display 62 and the operation part 64 serving as an interface.

As a preparation to breath holding of the object 1 during the collection of image data, the object 1 preferably inhales air with a high oxygen concentration (S216). This step is preferably performed in a similar manner to S204. When S204 is omitted, it is preferable to omit S216 as well. After that, the object 1 is caused to hold his/her breath (S218). The CPU 52 controls the scanner 20 through the scanner control unit 54, starts collecting image data according to the image data collection conditions having been set in S214 (S220), collects the image data on the object 1, obtains electrocardiographic data, and records the data in the data recorder 60. At the completion of the collection of image data (S222), the object 1 is caused to stop holding his/her breath (S224).

Since a setting may be made in S216 so as to collect image data in several times, the CPU 52 decides whether the scanning examination should be completed or not (S226). When the scanning examination is not completed and image data is repeatedly collected, it is preferable to allow the object 1 to take a rest, before returning to S216, to restore his/her physical condition including a heart rate to the resting condition (S228).

When it is decided in S226 that the scanning examination should be completed, the image data processing unit 56 and the electrocardiographic data processing unit 58 reconstruct the image based on the obtained image data and electrocardiographic data (S230) and record the image in the data recorder 60, so that the series of examinations is completed (S232).

Some of the steps in FIG. 2 will be discussed below in detail.

Figure 3:
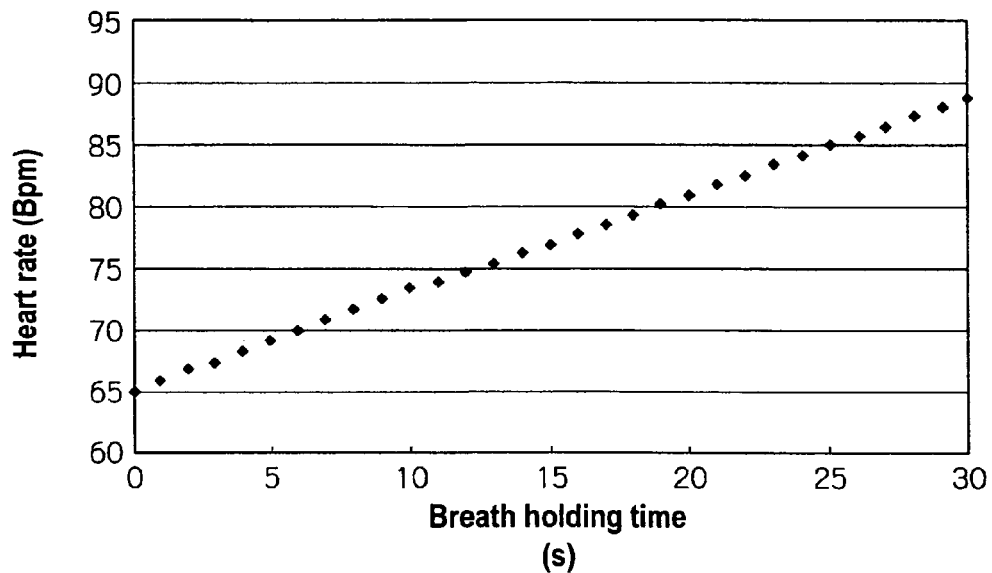
FIG. 3 is a graph showing an example of fluctuations in the heart rate of an object to be examined with time after the start of practice of breath holding.

First, the acquisition of electrocardiographic data during the practice of holding breath (S208) will be discussed below. In S208, for example, data is obtained as shown in FIG. 3 which indicates fluctuations in the heart rate of the object 1 with time from the start of the practice of holding breath (S206). In the example of FIG. 3, the heart rate is about 64 (beats/minute) at the start time of the practice of holding breath. With the lapse of breath holding time, the heart rate increases. The heart rate reaches about 89 after 30 seconds from the start of the practice of holding breath. The tendency of fluctuations in heart rate due to breath holding greatly vary among individuals, and the heart rate does not always increase in a monotonous manner but may decrease or fluctuate with the lapse of breath holding time. The electrocardiographic data processing unit 58 may have the function of estimating fluctuations in heart rate, for example, from 30 to 40 seconds of breath holding time based on data on fluctuations in heart rate until 30 seconds from the start of the practice of holding breath, according to a technique such as a linear approximation method. Further, the tendency of fluctuations in heart rate with the lapse of breath holding time may be recognized with higher accuracy by repeating the steps of S204 to S210 several times and determining an average of the obtained data on fluctuations in heart rate with time.

Figure 4:
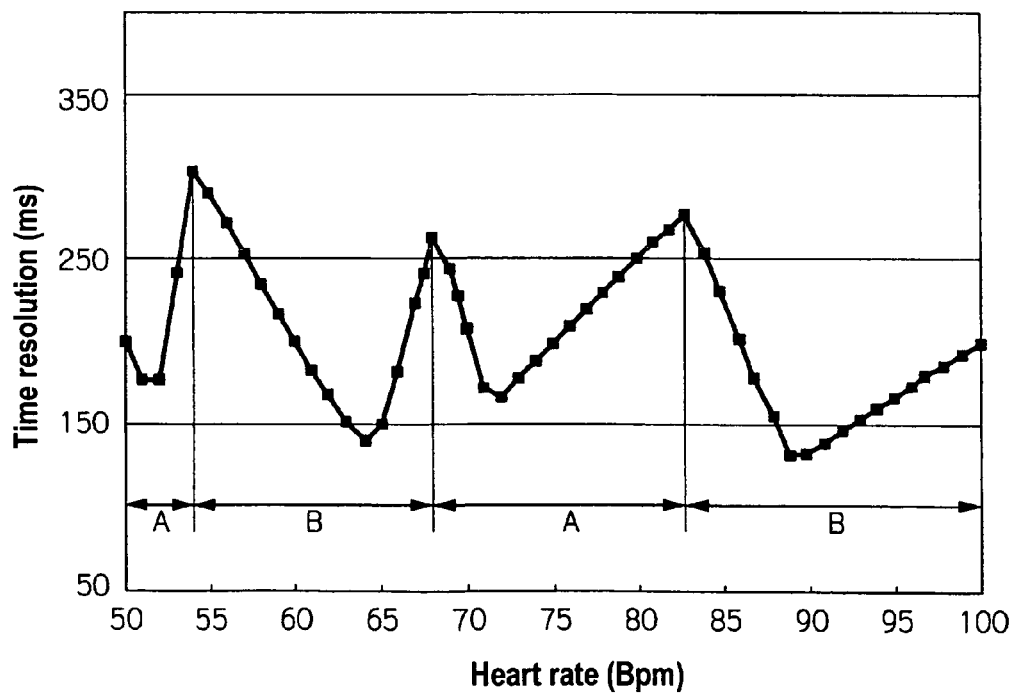
FIG. 4 is a graph showing the relationship among the time resolution of an image obtained by electrocardiographic synchronous scanning, image data collection conditions, and a heart rate.

The following will discuss the setting of the image data collection conditions based on the electrocardiographic data during the practice of holding breath (S214). FIG. 4 illustrates fluctuations in the time resolution of an image obtained by electrocardiographic synchronous scanning, relative to the image data collection conditions and the heart rate. FIG. 4 is a graph showing the relationship between the heart rate and the time resolution of an image when electrocardiographic synchronous scanning is performed using multislice CT according to segment reconstruction, in which two kinds of scan time are combined. In the present embodiment, segment reconstruction with four segments is used. The number of segments is not limited to four and any other number of segments is acceptable. In a range represented as A in FIG. 4, an image is reconstructed with scan time A. In a range represented as B in FIG. 4, an image is reconstructed with scan time B. The number of kinds of scan time is not limited to two. One or three or more kinds of scan time may be used.

The aforementioned "segment reconstruction" may be, for example, a technique disclosed in "Advanced Cardiovascular and Coronary CT" (Fumiko Kimura and six others), a paper on magazine "Image Diagnosis" (Volume 21, 2001, No. 12, pp. 1307-1317). In this technique, temporal window (corresponding to the time resolution of the present embodiment) is determined based on a difference between gantry one-rotation time GC (corresponding to the scan time of the present embodiment) and one cardiac cycle HC according to Equation 1 below:

$$\text{temporal window} = |GC - HC| \quad \text{[Equation 1]}$$

For example, when the heart rate is 64 (HC=60/64), scan time B (0.8 seconds) is more suitable than scan time A (1.0 second). An image obtained by segment reconstruction with scan time B (0.8) has a time resolution of |0.8−60/64|=0.138

(seconds), about 140 ms according to Equation 1. In the case of half reconstruction, data of 180°+fan angle 60°=240° is necessary and thus the number of segments at that time is determined by Equation 2 below:

The number of segments=240/360$GC$÷temporal window [Equation 2]

In the case where the numerical example is applied to Equation 2, Equation 3 is determined as below:

(240/360)×0.8÷0.138=3.9 [Equation 3]

Thus four segments can be reconstructed with a time resolution of 138 ms.

A heart rate even slightly larger than 64 reduces the time resolution (the numeric value increases). When the heart rate is 68, an image obtained in scan time B has a time resolution of about 270 ms. When the heart rate is larger than 68, an image obtained in scan time B further decreases in time resolution and an image obtained by image reconstruction in scan time A has a higher time resolution. Moreover, when the heart rate is larger than 83, scan time B is more suitable than scan time A. In this way, the time resolution of an image greatly varies with the heart rate.

Figure 5:
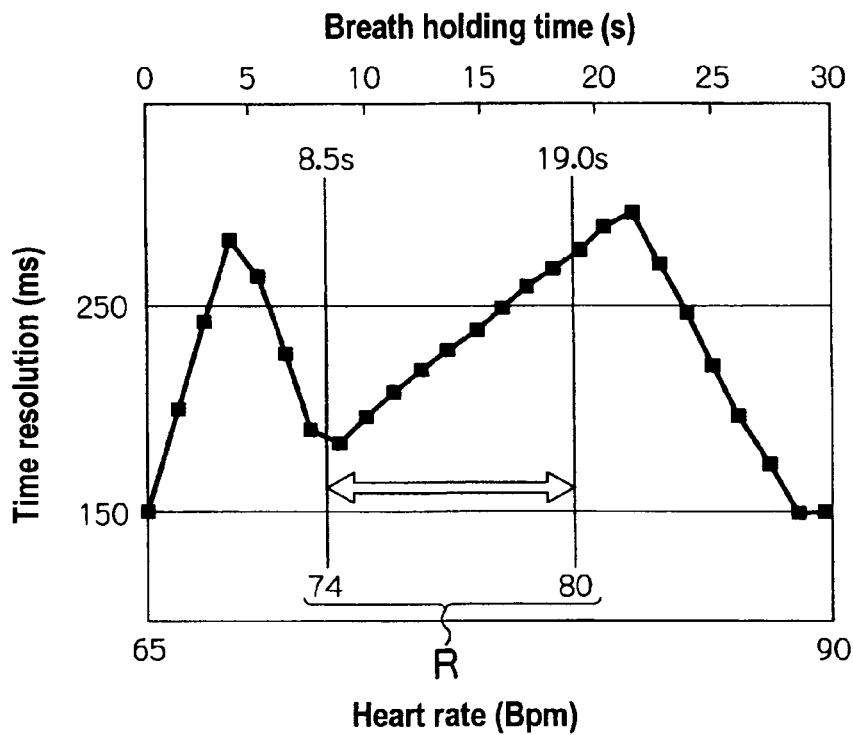
FIG. 5 is a time resolution graph showing estimated fluctuations in the time resolution of an image relative to a breath holding elapsed time.

In the following explanation, regarding the object 1 whose heart rate fluctuates with time as shown in FIG. 3 from the start of the practice of holding breath, electrocardiographic synchronous scanning is performed by segment reconstruction according to the relationship of FIG. 4 between the heart rate and the time resolution of an image. It is estimated from FIG. 3 that during the collection of image data, for example, the heart rate is about 64 at 0 seconds of breath holding time, that is, at the start time of breath holding, and the heart rate is about 74 at 10 seconds of breath holding time. As shown in FIG. 4, an image has a time resolution of about 140 ms at the heart rate of about 64, and an image has a time resolution of about 185 ms at the heart rate of about 74. As described above, based on data on fluctuations in heart rate with time during the practice of holding breath, it is possible to estimate breath holding time during the collection of image data and the relationship between the heart rate and the time resolution of an image. These relationships are illustrated in FIG. 5, which is a time resolution graph showing estimated fluctuations in the time resolution of an image relative to the breath holding time. The heart rate may be omitted in FIG. 5.

As is evident from FIG. 5, the time resolution of an image greatly varies with the breath holding time. When successively obtained images greatly fluctuate in time resolution, a problem may occur in the analysis of an image. Thus in the example of FIG. 5, a preferable time resolution is expected to stably change in a range from 8.5 to 19.0 seconds (the heart rate of 74 to 80) of the breath holding time and the range is recommended for the collection of image data (hereinafter, will be referred to as a recommended range). In other words, the image data collection conditions are preferably set such that the collection of image data is started 8.5 seconds after the start of breath holding and the collection of image data is completed by 19.0 seconds after the start of breath holding. Hence, in the present embodiment, the display 62 displays the time resolution graph of FIG. 5 and a recommended range marker R indicating the recommended range. Thus the operator can properly set the image data collection conditions with reference to the recommended range.

The recommended range may be automatically set by the CPU 52 according to a predetermined program. Alternatively, the range of time resolutions and the range of breath holding time may be set by the operator and the recommended range may be calculated according to the set range. The display of the recommended range is not limited to the example of FIG. 5. For example, the plot of the recommended range may be different from others in color, density, shape, size, and so on, or the plotted line of the recommended range may be displayed with a different color, density, width, and so on. Even when displaying only the time resolution graph on the display 62 without setting and displaying the recommended range, the operator can properly set the image data collection conditions with reference to the time resolution graph. A short breath holding time is preferable in consideration of the burden of the object 1. In some cases, the recommended range may be 22 to 30 seconds of the breath holding time in the example of FIG. 5.

In the case where image data is collected only within the recommended range, since an amount of data obtained at a time is limited, image data has to be repeatedly collected several times as described in S226 and S228 and the time of the scanning examination may be increased. However, an image with a preferable time resolution can be stably obtained in a well-planned way, and thus the exposure dose of the object 1 can be reduced.

Figure 6:
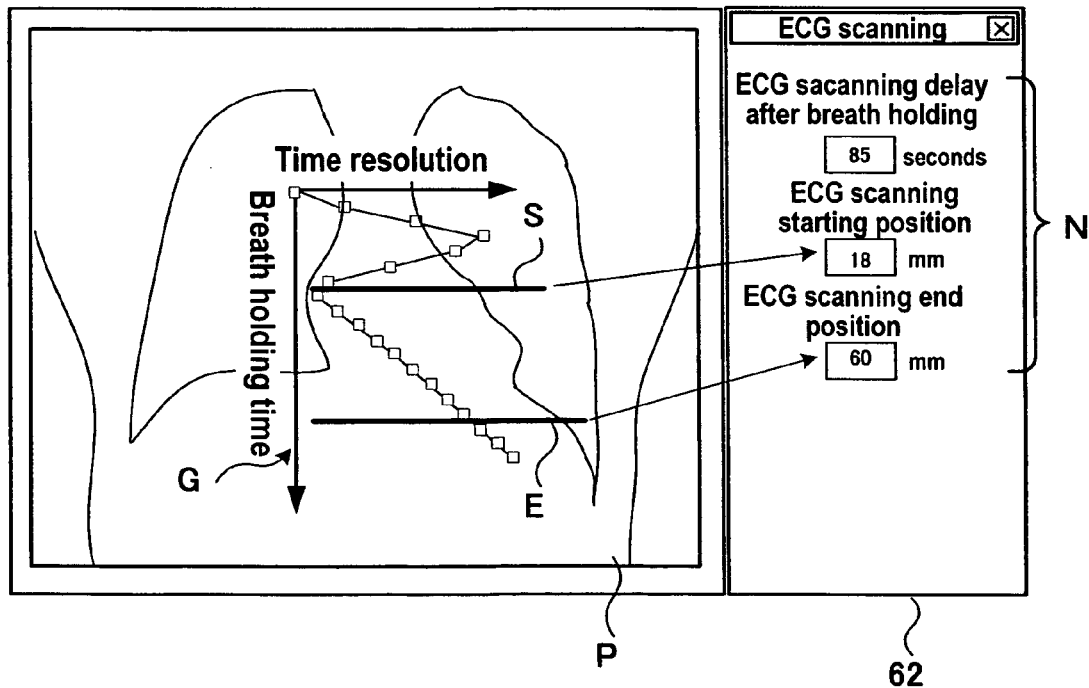
FIG. 6 is a diagram showing an example in which the projected image of the object and the time resolution graph are superimposed on the screen of a display.

When collecting image data on a plurality of parts of the object 1 while relatively moving the object table 24 and the scanner body 30 in the direction of the body axis, an elapsed time from the start time of image data collection varies with a distance from the starting position of image data collection on each part. The start time is the time when image data is collected on each part. In other words, image data on each part is collected at a different breath holding time, and thus images obtained on the respective parts have different time resolutions. Hence, in the present embodiment, the estimated time resolution of an image obtained on a part of the object 1 is clearly displayed as below:

FIG. 6 shows an example in which the projected image P of the object 1 in S212 and the time resolution graph G are superimposed on the screen of the display 62. In the time resolution graph G, fluctuations in estimated time resolution with time as described above are indicated on a coordinate system specified by the time axis and the temporal resolution axis. A start marker S indicates a planned start time of image data collection on the time resolution graph G and indicates a planned starting position of image data collection on the projected image P. In other words, image data collection is started at a time corresponding to the coordinates of the start marker S on the time axis of the time resolution graph G, and image data on a part of the object 1 is scheduled to be collected at that time, the part corresponding to the position of the start marker S on the projected image P. Similarly an end marker E indicates a planned end time of image data collection on the time resolution graph G and indicates a planned end position of image data collection on the image data collection position of the projected image P. With these markers, the relationship between a part where image data is collected on the object 1 and the breath holding time can be indicated. In this way, on the screen of the display 62, the positions of the projected image P and the origin of the time axis of the time resolution graph G and the direction and scale of the time axis are relatively adjusted, and the time resolution graph G and the position of image data collection on the projected image P are associated with each other, so that an estimated time resolution of an image obtained on a part of the object 1 can be clearly displayed.

Further, as shown in FIG. 6, an elapsed time from the start of breath holding to the start time of image data collection (ECG scanning delay after breath holding), a starting position of image data collection (ECG scanning starting position), and an end position of image data collection (ECG scanning end position) are preferably displayed on numerical display N according to the time resolution graph G and the positions of the start marker S and the end marker E.

The operator operates the operation part 64 to drag the start marker S and the end marker E which are displayed on the screen of the display 62. Thus the operator can move the start marker S and the end marker E relative to the projected image P and the time resolution graph G. The numerical display N is changed according to the movement. Further, the operator can directly change the numerical display N by operating the operation part 64. The start marker S and the end marker E are moved and displayed relative to the projected image P and the time resolution graph G according to the change.

Moreover, an image data collection range may be designated by inputting the positions of the start marker S and the end marker E on the projected image P or inputting numeric values on "ECG scanning starting position" and "ECG scanning end position" of the numerical display N.

In the example of FIG. 6, image data is scheduled to be collected around the upper end of the heart at 8.5 seconds of breath holding time. The best time resolution is expected at that time. This schedule is not changed even when the start marker S or the end marker E is moved. In the case of a particular image collection range like, for example, a part where coronary stenting is performed, it is particularly desirable that an image obtained in the image collection range have a preferable time resolution. Therefore, in the present embodiment, the image data collection conditions can be set so as to collect image data in the image collection range at a suitable time of image data collection. At that time, an estimated time resolution is in a suitable range.

Figure 7:
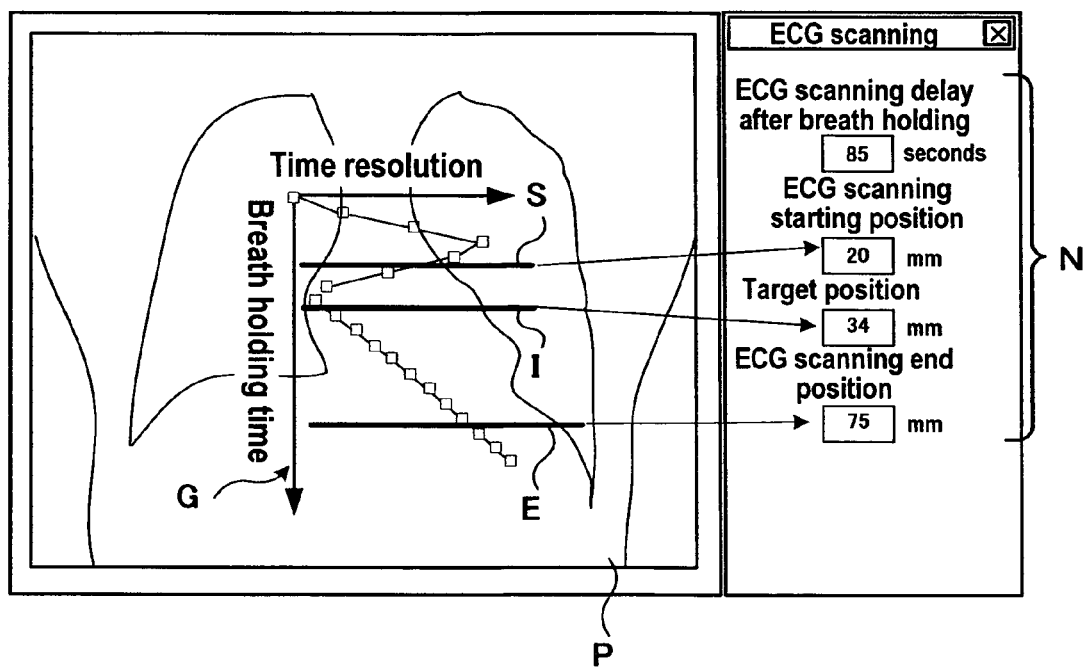
FIG. 7 is a diagram showing an example in which the time resolution graph of FIG. 6 is moved and displayed.

In FIG. 7, an image collection range marker I indicates a suitable time of image data collection on the time resolution graph G and indicates a range of image data collection on the projected image P. In other words, at a time corresponding to the coordinates of the image collection range marker I on the time axis of the time resolution graph G, image data on a part of the object 1 is scheduled to be collected, the part corresponding to the position of the image collection range marker I on the projected image P. An image obtained from the data is expected to have a suitable time resolution. As shown in FIG. 6, a point indicating the best time resolution among points on the time resolution graph may be used as an image collection range marker and it is not particularly necessary to display the image collection range marker.

The operator drags, through the operation part 64, the time resolution graph G displayed on the screen of the display 62, so that the operator can move the time resolution graph G and the image range marker I relative to the projected image P. While the operator only sets an image collection range on the projected image P by pointing or the like through the operation part 64, the time resolution graph G and the image collection range marker I may be moved accordingly relative to the projected image P. Further, the operator can directly change the numerical display N indicating the position of an image collection range by operating the operation part 64. According to the change, the time resolution graph G and the image collection range marker I are moved and displayed relative to the projected image P. The image data collection marker S and the image data collection end marker E are moved according to the movement of the time resolution graph G and the image collection range marker I. As shown in FIG. 6, some of the markers may be selected and moved.

In the example of FIG. 7, the time resolution graph G and the image collection range marker I are moved from the state of FIG. 6 without changing the position of the projected image P on the screen of the display 62. The projected image P may be moved without changing the positions of the time resolution graph G and the image collection range marker I on the screen of the display 62. In this case, the time resolution graph G and the image collection range marker I are fixed on the screen of the display 62, for example, at the center of the screen. When the operator drags the projected image P, scrolls the image, points an image collection range, and changes the numerical display N, the projected image P is moved and displayed relative to the time resolution graph G and the image collection range marker I.

In the example of FIG. 7, straight line I is displayed as the image collection range marker. The image collection range marker is not limited to a straight line. For example, the image collection range marker can be displayed as follows: a part expected to have a time resolution in a predetermined suitable range is displayed as a rectangle on the projected image P or the part is displayed with a different brightness or color from other parts. Although the image collection range marker I and the time resolution graph G are displayed in the example of FIG. 7, the display of the time resolution graph G may be omitted and only the image collection range marker may be displayed on the projected image P. Even in this case, it is possible to attain the purpose of the operator who wants to collect image data in the image collection range at the suitable time of image data collection.

In the examples of the time resolution graphs G shown in FIGS. 6 and 7, the breath holding start time is used as the origin of the time axis and the elapsed time of breath holding is used as time axis coordinates. The start time of image data collection may be used as the origin of the time axis and the elapsed time of image data collection may be used as time axis coordinates. The position of the origin of the temporal resolution axis and the direction and scale of the temporal resolution axis may be properly adjusted such that estimated fluctuations in time resolution with time can be easily read. For example, in FIGS. 5, 6 and 7, the time resolutions are used as temporal resolution axis coordinates. Thus as the number of numeric values increases in the direction of the temporal resolution axis, the time resolution decreases. In contrast, for example, when the reciprocals of time resolutions are used as temporal resolution axis coordinates, the time resolution improves as the number of numeric values increases in the direction of the temporal resolution axis.

When image data is collected (S220), the CPU 52 controls the scanner 20 through the scanner control unit 54 such that image data is collected according the settings of the image data collection start time and image data collection starting position which are indicated by the image data collection start marker S and the image data collection end time and image data collection end position which are indicated by the image data collection end marker E. First, the position of the object table 24 is adjusted such that image data is collected on the image data collection starting position of the object 1 at the image data collection start time. For example, the image data collection starting position of the object 1 and the image data collection position of the scanner body 30 may be aligned with each other before the start of breath holding (S218) and after the start of breath holding, image data collection may be started at the image data collection start time and the movement of the object table 24 may be started. Further, the image data collection starting position of the object 1 and the image data collection position of the scanner body 30 may be aligned with each other at the image data collection start time by aligning, for example, a part of the object 1 and the image data collection position of the scanner body 30 before the start of breath holding, and starting the movement of the object table 24 at the breath holding start time. The part is indicated by a point indicating the breath holding start time on the time resolution graph G in FIG. 6 or 7.

During the collection of image data, the object table 24 is moved at a speed keeping the relationship between the elapsed time of breath holding and the image data collection target part shown in FIG. 6 or 7. Thus the image collection range of the object 1 matches with the image data collection position of the scanner body 30 at the suitable time of image data collection and the range becomes a target of image data collection. The image data collection end part of the object 1 matches with the image data collection position of the scanner body 30 at the image data collection end time. The image data collection is completed thus (S222).

In the above embodiment, the object 1 and the scanner body 30 are relatively moved during the collection of image data. Image data may be collected by non-helical scan in which the object 1 and the scanner body 30 are not relatively moved. In this case, the image data collection start marker S and the image data collection end marker E are not necessary. Before the start of breath holding, a part of the object 1 and the image data collection position of the scanner body 30 are aligned with each other. The part of the object 1 is indicated by the image collection range marker. After the start of breath holding, image data is collected at a breath holding time indicated by the image collection range marker.

The method of moving the image data collection position of the scanner body 30 to change the image data collection part of the object 1 is not limited to the movement of the object table 24. The object table 24 may be fixed and the scanner body 30 may be moved. Alternatively, the image data collection position of the scanner body 30 may be moved.

In the above embodiment, fluctuations in heart rate when the object 1 holds his/her breath are analyzed. For example, fluctuations in heart rate are recorded when administering a medicine to the object 1 or stimulating the object 1, and fluctuations in heart rate and the time resolution of an obtained image at the administration of the medicine and the stimulation may be estimated during image data collection.

Embodiment 2

Figure 8:
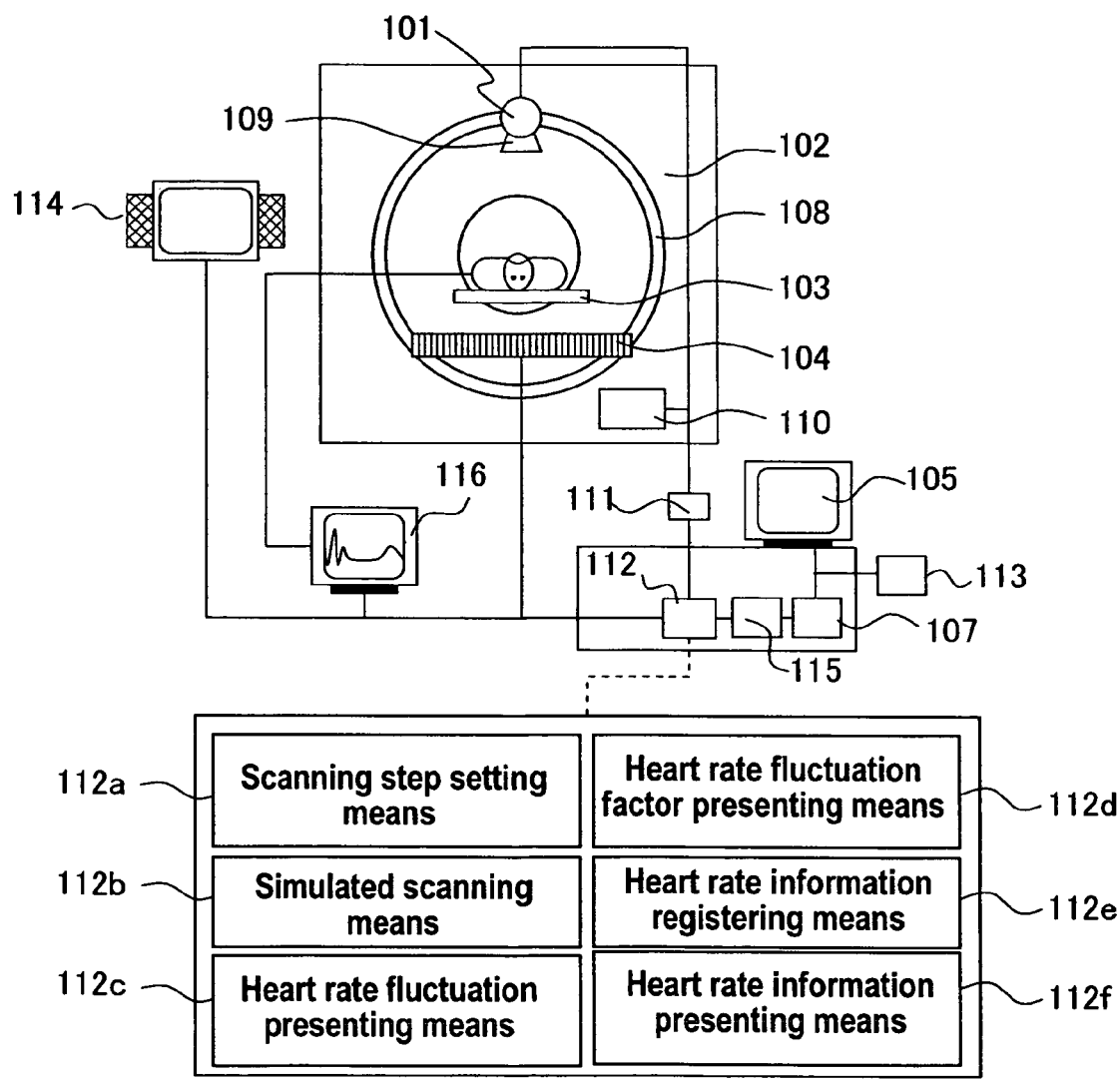
FIG. 8 is a block diagram showing an X-ray CT apparatus according to Embodiment 2.

FIG. 8 is a diagram showing the schematic configuration of an X-ray CT apparatus according to Embodiment 2. In FIG. 8, reference numeral 101 denotes an X-ray tube, reference numeral 102 denotes a scanner gantry, reference numeral 103 denotes an object table, reference numeral 104 denotes an X-ray detector, reference numeral 105 denotes a display, reference numeral 106 denotes an electrocardiograph, reference numeral 107 denotes an image processing device, reference numeral 108 denotes a rotary disc, reference numeral 109 denotes a collimator, reference numeral 110 denotes a rotary drive, reference numeral 111 denotes a measurement controller, reference numeral 112 denotes a computer, reference numeral 113 denotes an input device, and reference numeral 114 denotes a scanning information transfer unit.

The scanner gantry 102 emits and detects X-rays.

The image processing device 107 creates scanning data from measurement data having been detected by the scanner gantry 102, and converts the scanning data to a CT image signal.

The display 105 displays the CT image.

The scanner gantry 102 includes the rotary disc 108, the X-ray tube 101 mounted on the rotary disc 108, the collimator 109 which is mounted on the X-ray tube 101 and controls the direction of an X-ray flux, and the X-ray detector 104 mounted on the rotary disc 108. The rotary disc 108 is rotated by the rotary drive 110, and the rotary drive 110 is controlled by the measurement controller 111.

The intensity of an X-ray generated from the X-ray tube 101 is controlled by the measurement controller 111.

The measurement controller 111 controls the rotation of the rotary disc 108, X-ray radiation, and X-ray detection and the measurement controller 111 is operated by the computer 112.

Reference numeral 106 denotes periodic motion recognizing means for recognizing a periodic motion of the object.

In the following explanation, the periodic motion recognizing means 106 is an electrocardiograph.

The computer 112 acting as a controller prevents scanning in the event of excessive fluctuations in heart rate during scanning. Thus the heart can be imaged with the optimum time resolution.

The present embodiment will be described below in accordance with the accompanying drawings.

The computer 112 includes scanning step setting means 112a, simulated scanning means 112b, heart rate fluctuation presenting means 112c, heart rate fluctuation factor presenting means 112d, heart rate information registering means 112e, and heart rate information presenting means 112f.

The scanning step setting means 112a sets the steps of scanning the heart.

The simulated scanning means 112b performs simulated scanning (simulated training) according to the scanning steps set by the scanning step setting means 112a.

The heart rate fluctuation presenting means 112c presents fluctuations in heart rate during scanning of the heart or simulated scanning to the operator through the display 115.

The heart rate fluctuation factor presenting means 112d presents information on a cause of fluctuations in heart rate to the object through the scanning information transfer unit 114 during scanning of the heart or simulated scanning.

The heart rate information registering means 112e registers the tendency of fluctuations in heart rate in a storage device 115, the tendency having being determined during scanning of the heart.

The heart rate information presenting means 112f searches heart rate information registered in the storage device 115 for the tendency of fluctuations in the heart rate of the object who is a target of heart scanning, and presents the tendency to the operator through the display 105. The following will discuss factors changing the heart rate.

The following is factors changing the heart rate during scanning.

(1) Breath holding during scanning

Breath holding is performed to prevent motion artifact caused by respiration. However, continued breath holding increases the heart rate, causing fluctuations in heart rate.

(2) A factor relates to the operations of a CT apparatus, for example, vibrations occurring when a bed moves, a rotating sound of a scanner, or the like. These operations make the object feel nervous, causing fluctuations in heart rate.

(3) A factor relates to a scanning technique, for example, injection of a contrast medium. The injection of a contrast medium makes the object feel uncomfortable, causing fluctuations in heart rate.

In the present embodiment, as a method of eliminating the heart rate fluctuation factors, simulated scanning is performed before scanning through the same steps as scanning without X-ray irradiation.

(A) The simulated scanning allows the object to practice holding his/her breath, preventing the heart rate from fluctuating due to breath holding.

(B) Before scanning, the object actually experiences a rotating sound of a scanner and vibrations of a bed as in scanning, relieving tension to scanning. Further, it is possible to prevent the heart rate of the object from fluctuating due to the operations of the CT apparatus.

(C) Another means of eliminating heart rate fluctuation factors is to present heart rate fluctuation factors estimated during scanning to the object beforehand. Before operations acting as heart rate fluctuation factors including the start of rotation of the scanner, the start of movement of the bed, and the start of injection of a contrast medium, the object is informed of the factors beforehand through sound or a monitor, so that the object can feel relaxed about scanning and the heart rate can be prevented from fluctuating due to the operations of the CT apparatus.

(D) In the simulated scanning, the same steps as actual scanning of the heart are performed except for X-ray irradiation, and thus fluctuations in the heart rate of the object during scanning of the heart can be estimated by observing fluctuations in the heart rate of the object during simulated scanning.

Figure 9:
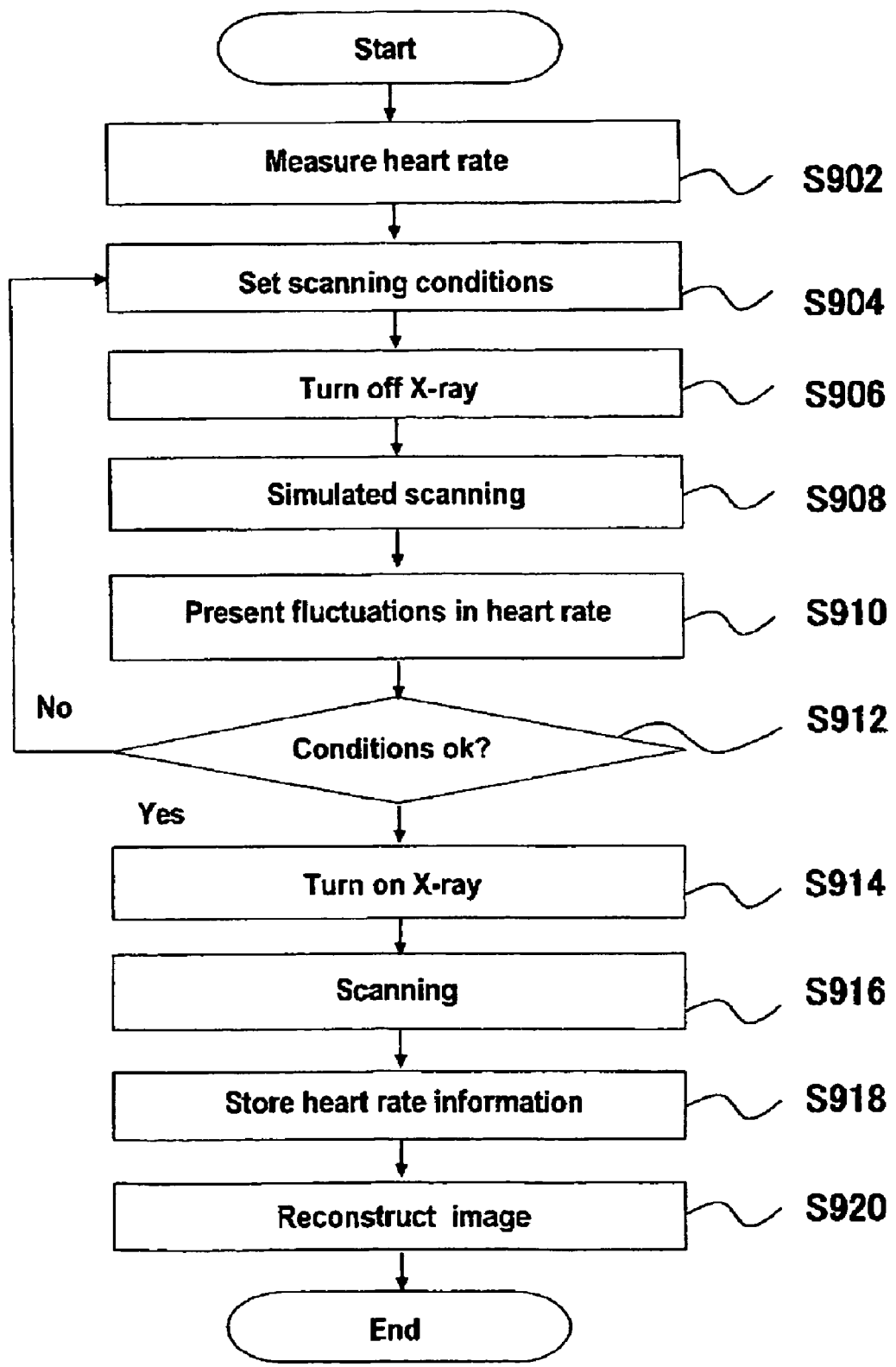
FIG. 9 is a flowchart showing processing for obtaining a tomogram by means of the ray CT apparatus shown in FIG. 8.

FIG. 9 is a flowchart showing a procedure until an image of the heart is created with the optimum time resolution by using the X-ray CT apparatus to prevent fluctuations in heart rate.

The following will discuss the processing steps of FIG. 9.

In step S900, the scanning of the heart is started.

In step S902, an electrocardiograph 6 is used to measure the heart rate of the object who is a target of scanning.

In step S904, based on the heart rate having been measured in step S902, the scanning step setting means 112a determines scanning conditions necessary for scanning the heart and the scanning steps including the presence or absence of the injection of a contrast medium. The scanning conditions include the rotation speed of the rotary disc 108, the traveling speed of the object table 203, a scanning range, a tube current, and a tube voltage.

The scanning conditions and scanning steps can be corrected by the operator through the input device 113.

In step S906, the output of the X-ray tube 101 is turned off to stop X-ray irradiation.

In step S908, the simulated scanning means 112b performs simulated scanning according to the scanning conditions having been determined in step S904. The steps of simulated scanning are similar to those of actual scanning of the heart except for the absence of X-ray irradiation.

At this point, the heart rate fluctuation factor presenting means 112d presents heart rate fluctuation factors to the object through the scanning information transfer unit 114.

FIG. 10 shows an example of heart rate fluctuation factors displayed on the scanning information transfer unit 114.

First, the upper part of the screen shows that scanning training is underway, that is, simulated scanning is performed.

A chart at the center of the screen indicates heart rate fluctuation factors presented to the object.

This chart is divided into scanning steps including "preparation for scanning", "contrast imaging", and "scanning."

Further, in order to visualize the scanning step in progress, the step in progress is clearly displayed by coloring, blinking, shading, and so on. In FIG. 10, the step of "preparation for scanning" is shaded, which indicates that "preparation for scanning" is currently performed.

The heart rate fluctuation factors may be conveyed to the object as sound through acoustic equipment installed in the scanning information transfer unit 114.

In step S910, the heart rate fluctuation presenting means 112c presents fluctuations in heart rate to the operator through the display 105. The fluctuations in heart rate have been measured by the electrocardiograph 106 during simulated scanning.

FIG. 11 shows an example of fluctuations in heart rate on the display 105.

The horizontal axis represents an elapsed time from the start of scanning and the vertical axis represents the heart rate of the object.

In FIG. 11, a solid line indicates fluctuations in heart rate and also indicates the times of heart rate fluctuation factors including "the movement of the bed", "the rotation of the gantry", and "breath holding".

In FIG. 11, broken lines indicate a heart rate area enabling a desired time resolution.

The operator can set the heart rate area beforehand.

As described above, in the case of electrocardiographic synchronous reconstruction, a time resolution determined by a combination of the heart rate of the object, a scan time, and a scanning speed during scanning changes with fluctuations in heart rate.

The heart rate fluctuation presenting means 112c calculates a heart rate range enabling a desired time resolution and displays the range on the display 105, based on a time resolution which is desired by the operator and inputted through the input device 113 and the scan time determined in step S904.

Alternatively, in order to achieve a desired time resolution, a combination of a change in heart rate as a periodic motion and a scan time or the table moving speed serving as a scanning speed may be calculated and displayed. In this case, the calculation is performed by the heart rate information presenting means 112f.

In step S912, when the operator decides that an expected time resolution can be obtained based on the fluctuations in heart rate in step S910, the process advances to the subsequent step.

When the operator decides that an expected time resolution cannot be obtained, the process returns to step S904, and then steps S904 to S908 are repeatedly performed.

The steps of simulated scanning are completed thus.

In step S914, the output of the X-ray tube 1 is turned on to enable X-ray irradiation.

In step S916, scanning is performed according to the scanning conditions having been determined in step S904.

At this point, the heart rate fluctuation factor presenting means 112d presents, as in step S908, heart rate fluctuation factors to the object through the scanning information transfer unit 114.

In step S918, the heart rate information registering means 112e registers, in the storage device 115, heart rate information on the object based on the heart rate having been measured by an electrocardiograph 116 in step S916.

FIG. 12 shows an example of heart rate information registered in the storage device 115. The heart rate information is registered so as to correspond to an object ID and an object's name. The items of the heart rate information include an increase/decrease in heart rate due to breath holding, and an increase/decrease in heart rate due to contrast imaging. The time series variations in heart rate during simulated scanning may be registered as a graph which indicates specific fluctuations in heart rate. In this case, a heart rate fluctuation factor start time such as a breath holding start time and a contrast imaging start time may be registered. In FIG. 12, a breath holding start time is represented as "Brth" and a contrast imaging start time is represented as "Cnt". When the heart of the object is imaged two or more times, heart rate information on the number of times of scanning may be registered. Further, the maximum breath holding time of the object may be registered as heart rate information.

In step S920, the image processing device 117 reconstructs a tomogram of the heart based on scanning data having been obtained from the electrocardiograph 116 and the X-ray detector 203. Image reconstruction using electrocardiographic information is performed by applying retrospective ECG gate scanning to spiral scan, for example, in a multislice X-ray CT apparatus, interpolating discontinuous projected data at that time by using, for example, data on heartbeat phases opposed 180° to reduce motion artifact, forming projection data on a given slice position and with a given heart phase by using consecutive divided projection data obtained thus, and combining or synthesizing the data when necessary.

The heart rate information having been registered by the heart rate information registering means 112e in step S918 is used in the subsequent scanning of the same object.

When the subsequent scanning is performed according to the flow of FIG. 9, the heart rate information presenting means 112f presents, on the display 105 in step S904, heart rate information on the object who is a target of scanning.

FIG. 13 shows an example of presented heart rate information. Items of presented heart rate information include the number of times the heart rate is increased/stabilized/reduced by breath holding, the number of times being calculated according to the tendency of fluctuations in heart rate before scanning, a mean value of heart rate fluctuations caused by breath holding, the number of times the heart rate is increased/stabilized/reduced by administering a contrast medium, a mean value of heart rate fluctuations caused by administration of a contrast medium, and a mean value of breath holding times.

Heart rate information on the past scanning is presented to the operator when the scanning conditions are set in step S904, so that the operator can set the scanning conditions so as to have the optimum resolution with high efficiency. Further, an scanning range can be easily determined. The scanning range is determined by deciding the breath holding time of the object.

Embodiment 3

Figure 14:
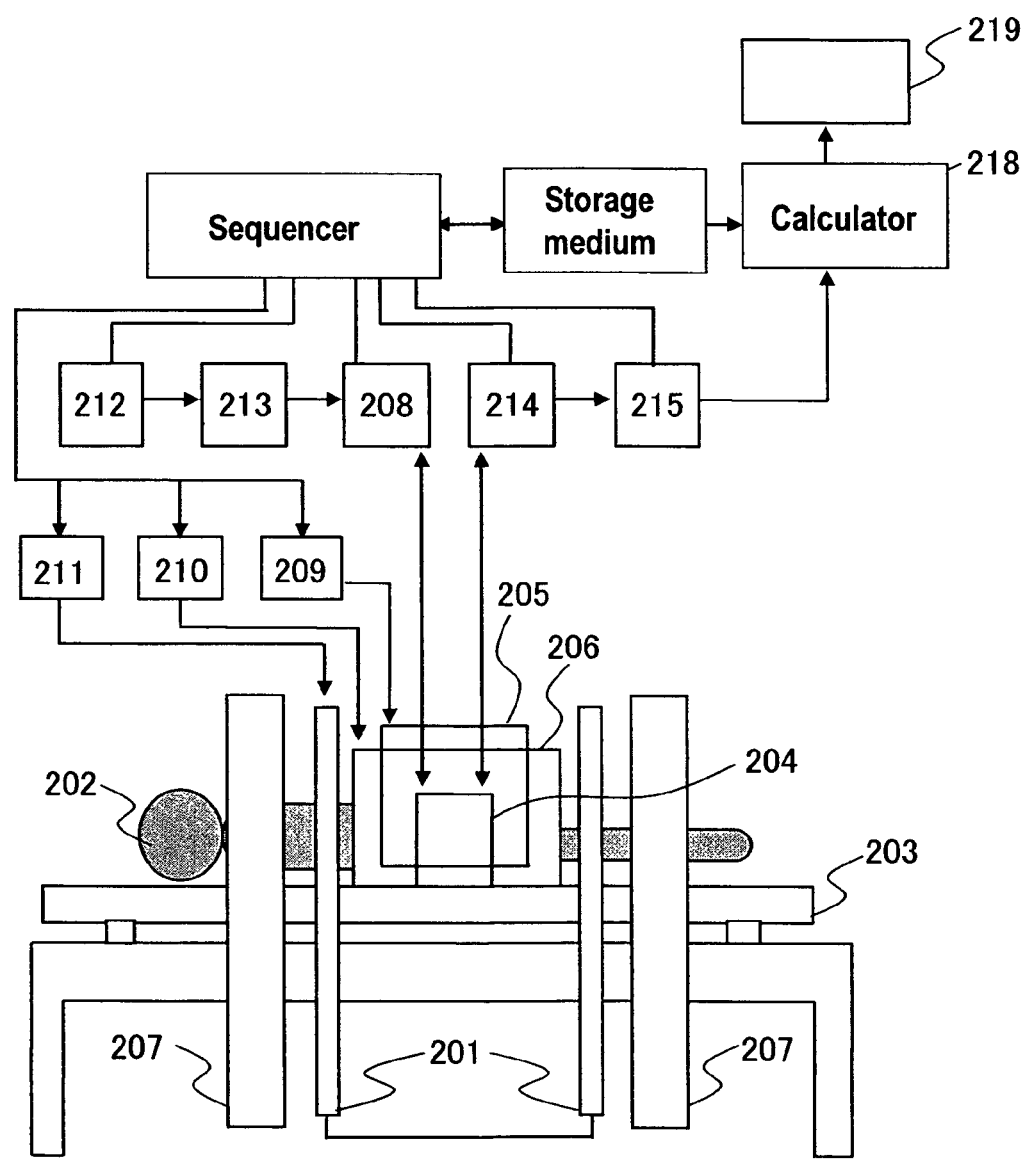
FIG. 14 is a block diagram showing an MRI apparatus according to Embodiment 3.

FIG. 14 is a diagram showing the outline of an MRI apparatus according to Embodiment 3. The MRI apparatus includes a magnet 201 for generating a uniform static magnetic field in a space where an object 202 such as a patient is laid, a bed 203 for carrying the object 202 into the space, an RF coil 204 for emitting a high-frequency magnetic field to the object and detecting a nuclear magnetic resonance signal (echo signal) generated from the object, gradient magnetic field generating coils 205, 206, and 207 for generating magnetic field gradients in x direction, y direction, and z direction in a static magnetic field, and a control system for controlling these operations. FIG. 14 shows a horizontal magnetic field MRI apparatus which uses a magnet for generating a static magnetic field in the body axis direction (horizontal direction) of the object. A vertical magnetic field MRI may be used which generates a static magnetic field perpendicularly to the body axis direction. The RF coil 204 emits a high-frequency magnetic field and detects an echo signal. These functions may be separated from each other.

The RF coil 204 for two uses in FIG. 14 is connected to a high-frequency magnetic field transmitting unit and a high-frequency magnetic field receiving unit via a switching circuit (not shown). The high-frequency magnetic field transmitting unit is mainly made up of a synthesizer 212 for generating a high frequency signal of a predetermined frequency, a modulation circuit 213 for modulating the high frequency signal generated by the synthesizer 212 to a signal with a predetermined envelope, and a high frequency power supply 208 for supplying power to the RF coil 204. The high-frequency magnetic field receiving unit is made up of an amplifier 214 and a receiver 215 including a quadrature detector circuit and an AD converter. The gradient magnetic field generating coils 205, 206, and 207 in three directions are connected to power supplies 209, 2210, and 211, respectively. The operations of the gradient magnetic field power supplies 209, 210, and 211, the high-frequency magnetic field transmitting unit, and the high-frequency magnetic field receiving unit are controlled by the control system according to a timing chart called a pulse sequence. The control system includes a calculator 218 which performs kinds of calculations including a correction and Fourier transform on a measured echo signal and controls the overall apparatus, a display 219 which displays an image and a spectrum or the like as a calculation result and displays a GUI for enabling input from the user, a storage device 217 which stores data necessary for the calculation of the calculator 218 and calculated data, and a sequencer 216 for controlling the gradient magnetic field power supplies 209, 210, and 211, the high-frequency magnetic field transmitting unit, and the high-frequency magnetic field receiving unit in response to a command of the calculator 218 according to a previously selected pulse sequence. The calculator 218 includes an input device (not shown). The calculator 218 can register an object, make a call, select a pulse sequence according to a scanning method, and input a scanning parameter.

Figure 15A:
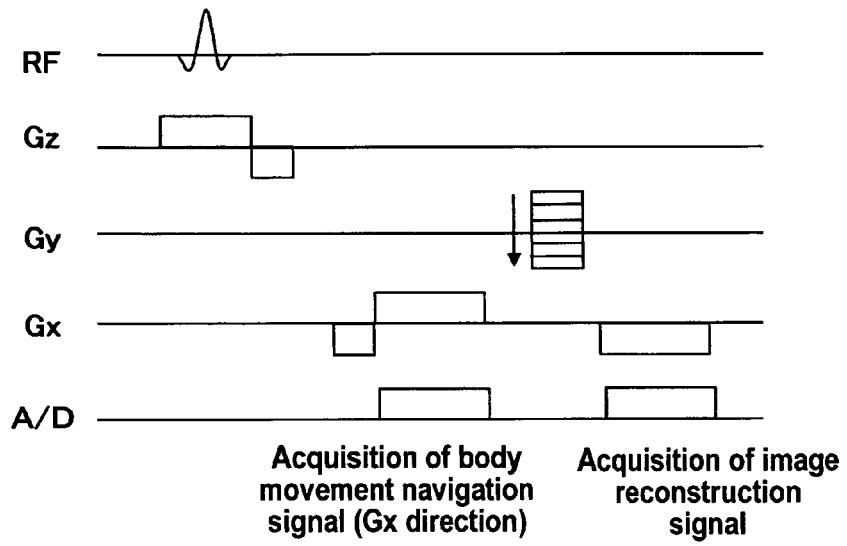
FIG. 15(*a*) is a schematic diagram showing an example of a body movement navigation sequence.
Figure 15B:
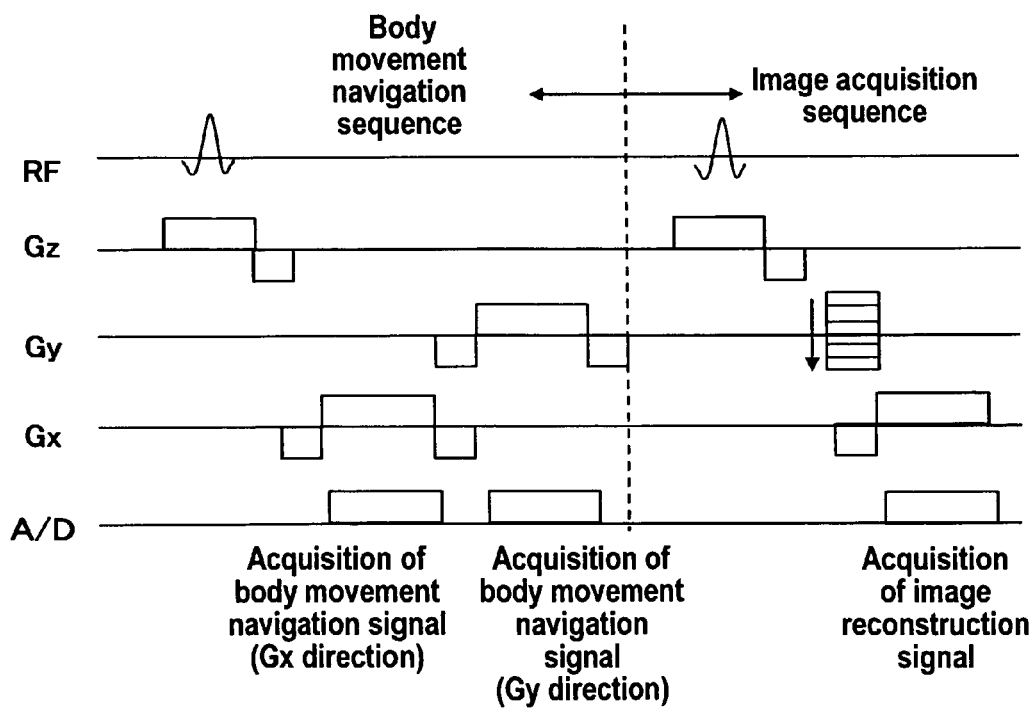

In the MRI apparatus according to the present embodiment, a signal reflecting body movement information, that is, a body movement navigation echo is used as periodic motion data recording means. To be specific, prior to the acquisition of an image reconstruction signal, a body movement navigation signal is obtained and a correction is made such that a body movement component of the subsequently obtained image reconstruction signal is removed from position information (phase information) included in the body movement navigation signal. FIG. 15 shows an example of the body movement navigation sequence. In the body movement navigation sequence of FIG. 15(a), after a slice to be imaged is first selected and excited, phase encoding is not added but a gradient magnetic field of one direction (in this case, a reading gradient magnetic field Gx) is applied to measure the navigation signal, and then the image reconstruction signal is obtained while phase encode is added. In this sequence, the body movement can be corrected in X direction. In a body movement navigation sequence of FIG. 15(b), an RF excitation pulse and a slice are selected to detect the body movement navigation echo and an RF excitation pulse and a slice are selected to detect the image reconstruction signal in a separated manner, and amounts of movement in two directions are detected using gradient magnetic fields in two directions (in this case, a reading-direction gradient magnetic field Gx and a phase-encoding direction gradient magnetic field Gy). Thus a body movement can be corrected in the plane of the slice.

In Embodiment 3, prior to MRI scanning of the object, simulated MRI scanning is performed to obtain the body movement navigation echo signal. Then, a time resolution is estimated based on the body movement navigation echo signal having been obtained in simulated scanning, and image data is collected in an image collection range (a part to be imaged) at a time suitable for image collection.

By using an image data collection system including the X-ray CT apparatus or the MRI apparatus according to Embodiments 1 to 3, the object may be imaged before and after injection of a contrast medium, and a pair of images obtained before and after injection of the contrast medium may be discriminated from each other to generate a differential image. In this case, simulation training may be provided to the object having been injected with a contrast medium and a time resolution may be estimated based on periodic motion data (heart rate) having been obtained in the simulation training. Therefore, image data collection can be controlled in consideration of the influence of a contrast medium on the periodic motion of the object.

INDUSTRIAL APPLICABILITY

When a part of a periodically moving object is scanning by a medical imaging apparatus, periodic motion data is obtained before the scanning, and the scanning time of the target part is determined based on the periodic motion data, so that a medical image can be obtained with less motion artifact.

The invention claimed is:

1. An image data collection system for collecting image data in an image data collection range including a periodically moving part of an object to be examined, the system comprising:
a device for displaying a graph indicating fluctuations in an estimated time resolution of an image obtained on a part of the object with time information with a projected image of the object, in advance of image data collection, wherein the time information in the graph is associated with position of the image data collection on the projected image of the object.

2. An image data collection control method for collecting multiple pieces of image data from an image data collection range including a periodically moving part of an object to be examined, the method comprising:
a step of obtaining periodic motion data indicating a change of a periodic motion with time;
a step of obtaining a time range so that the time resolution is within the desired range on an image data collection condition based on the periodic motion data and a relationship among a time resolution of an image obtained, image data collection conditions and periodic motion;
a step of setting on a body axis of the object (i) a starting position of image data collection and (ii) an end position of image data collection such that the time range matches the image data collection range between the set start position and the set end position; and
a step of collecting the image data collection from the image data collection starting position to the end position.

3. The image data collection control method according to claim 2, further comprising:
a projected image obtaining step of obtaining a projected image of the object, and
an image data collection range designating step of designating the image data collection range based on the projected image.

4. The image data collection control method according to claim 3, wherein in the image data collection range designating step, the image data collection range is designated by designating a starting position and an end position of collection of the image data in the projected image.

5. The image data collection control method according to claim 3, wherein the image data collection condition setting step includes, before the image data collection range designating step, a time resolution estimating step of estimating a fluctuation in a time resolution of the image data with time based on the periodic motion data, and
in the image data collection range designating step, a time resolution graph and the projected image are superimposed on each other, the time resolution graph indicating the fluctuation in the time resolution of the image data with time.

6. The image data collection control method according to claim 5, wherein in the image data collection range designating step, the desired time resolution range in the time resolution graph is superimposed so as to correspond to the image data collection range in the projected image.

7. The image data collection control method according to claim 5, wherein in the time resolution graph, at least points ranging from a start point corresponding to a start time of image data collection in the time resolution graph to an end point corresponding to a stop time of image data collection are respectively superimposed on positions ranging from a starting position to an end position of image data collection in the projected image.

8. The image data collection control method according to claim 5, wherein in the image data collection range designating step, input is received for designating or changing at least one of a position of the time resolution graph and a position of a part of the graph, and at least one of the image data collection range and the desired time resolution range is designated or changed based on the input.

9. The image data collection control method according to claim 5, wherein in the image data collection range designating step, a numeric value indicating a position on the projected image is displayed, the position corresponding to at least one of points of the time resolution graph, input is received to change the numeric value, and relative positions of the time resolution graph, at least one of the points of the graph, and the projected image are changed based on the input.

10. The image data collection control method according to claim 5, wherein in the image data collection position control step, the image data collection range and the image data collection position are relatively moved so as to keep a positional relationship between an elapsed time in the time resolution graph and the image data collection range in the projected image, and
the relative movement and the image data collecting step are simultaneously performed.

11. The image data collection control method according to claim 1, further comprising:
a step of determining a suitable change of the periodic motion data such that the image data of the image data collection range has the time resolution within the desired range, and
a step of displaying a change of the periodic motion data with time and the suitable change.

12. The image data collection control method according to claim 11, wherein a combination of the suitable change and a speed of the relative movement is calculated in the image data collection condition setting step, and the image data collection range and a collection position of the image data are relatively moved in the image data collection position control step.

13. The image data collection control method according to claim 11, wherein the periodic motion data obtaining step is repeated until the change of the periodic motion data falls below a predetermined value.

14. An image data collection system for collecting multiple pieces of image data from an image data collection range including a periodically moving part of an object to be examined, the system comprising:

a periodic motion data obtaining means for obtaining periodic motion data indicating a change of a periodic motion with time;

an image data collection condition setting means for obtaining a time range so that the time resolution is within the desired range on an image data collection condition based on the periodic motion data and a relationship among a time resolution of an image obtained, image data collection conditions and periodic motion;

an image data collection position control means for setting on a body axis of the object (i) a starting position of image data collection and (ii) an end position of image data collection such that the time range matches the image data collection range between the set start position and the set end position; and an image data collecting means for collecting the image data collection from the image data collection starting position to the end position.

15. The image data collection system according to claim 14, wherein the image data collection condition setting means estimates a fluctuation in the time resolution of the image data with time based on the periodic motion data before designating the image data collection range, and the image data collection condition setting means superimposes a time resolution graph and the projected image, the time resolution graph indicating the fluctuation in the time resolution of the image data.

16. The image data collection system according to claim 14, wherein the image data collecting means is an X-ray CT apparatus comprising:

an X-ray source for emitting an X-ray, an X-ray detector which is opposed to the X-ray source with the object being interposed between the X-ray source and the X-ray detector and detects the X-ray to output X-ray transmission data, a rotating means capable of rotating with the X-ray source and the X-ray detector, a table on which the object is laid, a table controller for controlling a table moving speed for moving the table, an image processing means for generating a tomogram of the object based on the X-ray transmission data, and a display means for displaying the tomogram, the periodic motion data obtaining means is a heart rate meter for measuring and obtaining a heart rate of the object, the image data collection condition setting means calculates a combination of a change of the periodic motion data and the table moving speed to obtain the desired time resolution, and the table controller moves the table according to the table moving speed.

* * * * *